United States Patent [19]

Strandberg, Jr. et al.

[11] 4,156,843

[45] May 29, 1979

[54] MICROWAVE MOISTURE INDICATOR AND CONTROL

[75] Inventors: Charles F. Strandberg, Jr., High Point; Robert C. Strandberg, Greensboro, both of N.C.

[73] Assignee: Strandberg Engineering Laboratories, Inc., Greensboro, N.C.

[21] Appl. No.: 886,097

[22] Filed: Mar. 13, 1978

[51] Int. Cl.$^2$ .......................................... G01R 27/04
[52] U.S. Cl. .............................................. 324/58.5 B
[58] Field of Search ............ 324/58.5 B, 58 B, 58.5 A

[56] References Cited

U.S. PATENT DOCUMENTS

| | | | |
|---|---|---|---|
| 3,133,246 | 5/1964 | Jaffee et al. | 324/58.5 B |
| 3,144,601 | 8/1964 | Slabodsky | 324/58.5 B |
| 3,490,037 | 1/1970 | Williams | 324/58.5 B |
| 3,534,260 | 10/1970 | Walker | 324/58.5 A |
| 3,593,136 | 7/1971 | Chapman et al. | 324/58.5 B X |
| 3,639,834 | 2/1972 | Walker | 324/58.5 B |
| 3,693,079 | 9/1972 | Walker | 324/58.5 A |
| 3,913,012 | 10/1975 | Kujath | 324/58.5 A |
| 4,052,666 | 10/1977 | Auer et al. | 324/58.5 B |

FOREIGN PATENT DOCUMENTS

| | | | |
|---|---|---|---|
| 1052250 | 12/1966 | United Kingdom | 324/58.5 B |
| 211856 | 1968 | U.S.S.R. | 324/58.5 B |
| 247513 | 1970 | U.S.S.R. | 324/58.5 B |

Primary Examiner—Stanley T. Krawczewicz

[57] ABSTRACT

A moisture indicator and control device for measuring the moisture content of a moving web includes a modulated signal microwave generator, directional microwave transmitter and receiver antenna horns which are angularly mounted with respect to each other on one side of a moving web of material whose moisture content is being monitored. The transmitter and receiver horns are mounted within an enclosure with their adjacent edges in physical contact and with a selected optimum angle between them to minimize residual energy transfer from the transmitter horn into the receiver horn. Sine wave modulated microwaves are transmitted by the transmitter horn toward the web at a selected angle of incidence thereto. A portion of the modulated microwave signal is reflected by the web and is received by the tranmsmitter horn. The microwave detector in the base of the receiver horn detects the reflected microwave signal and produces a sine wave output, the amplitude of which is directly proportional to the amount of moisture present in the web. The moisture indicator circuit includes in connected series an operational amplifier whose gain is adjustable over a wide range for amplifying the detected signal, an a-c to d-c convertor for converting the a-c detected signal to d-c, a d-c amplifier whose gain is controlled by a range potentiometer and a microammeter moisture meter. The device further includes a special offsetting circuit to offset any signal present when no material is in front of the transmitter horn, an over range indicator, and moisture control circuit for providing correctional control signals for restoring the moisture content of the web to a selected level.

12 Claims, 4 Drawing Figures

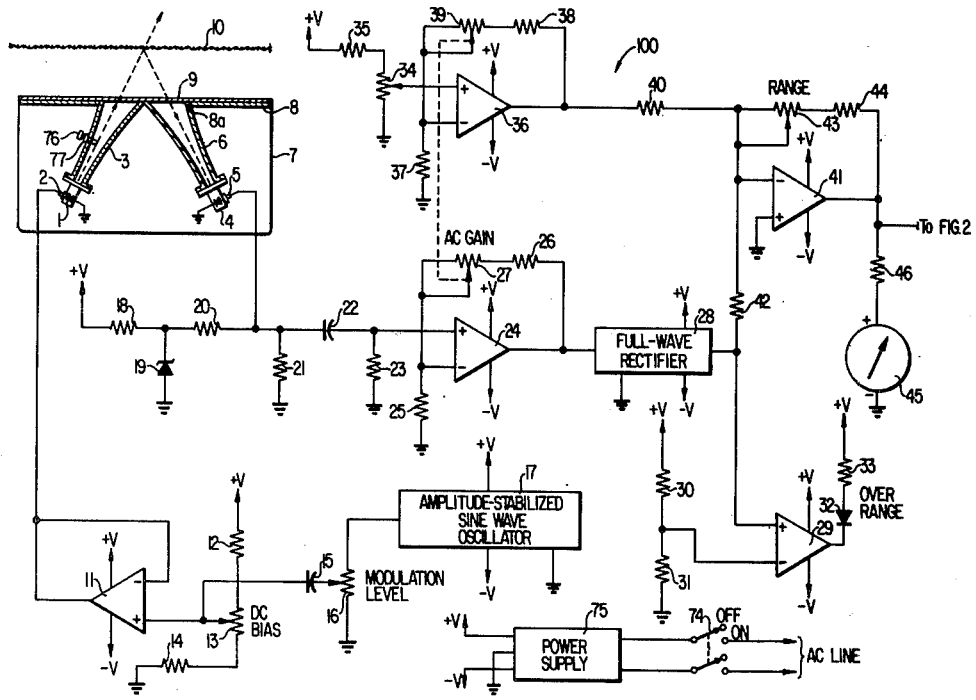

MICROWAVE MOISTURE INDICATOR AND CONTROL

BACKGROUND OF INVENTION

1. Field of the Invention

The invention relates to an improved microwave moisture indicator and control device and more particularly to a microwave moisture indicator which directs microwaves obliquely toward a web of material and detects microwaves reflected from the web of material, the detected signal being proportional to the moisture content of the web of material.

2. Description of the Prior Art

Microwave moisture measuring devices are broadly old in the art as indicated by the following patents known to applicants:

U.S. Pat. No. 3,534,260
U.S. Pat. No. 3,639,834
U.S. Pat. No. 3,913,012
Gt. Britain Pat. No. 1,052,250

The present invention utilizes the principle that microwave energy reflected from a sheet or web of material is highly dependent upon the moisture content of the material. Thus, according to this invention modulated microwave signals are directed toward a web at a selected optimum angle of incidence, and only that part of the microwave signal which is reflected by the web is detected and measured.

The closest prior art device knwon to applicants which utilizes the principle identified in the preceding paragraph and thus which measures only that part of the microwave signal which is reflected by the web is British Pat. No. 1,052,250.

U.S. Pat. No. 3,534,260 and 3,639,834 each disclose microwave moisture measuring systems which direct microwaves through a sheet of material, such as paper, reflect the microwaves back through the sheet and detect the microwaves on the same side of the sheet from which the microwaves were transmitted. A portion of the microwave energy is absorbed each time it passes through the web. The measurements made by the apparatus disclosed in U.S. Pat. Nos. 3,534,260 and 3,639,834 is a function of the attentuation of the microwave energy transmitted through the web. As recognized by British Pat. No. 1,052,250, a disadvantage of the process representedby U.S. Pat. Nos. 3,534,260 and 3,639,834 is that the web moisture content is only very slightly dependent upon the absorbed microwave energy, thus large differences in moisture give only slight differences in absorption, so that measurement is inaccurate.

U.S. Pat. No. 3,913,012 discloses a microwave moisture measuring system whose measurement is dependent upon the microwave absorbtivity of a workpiece. The system disclosed in U.S. Pat. No. 3,913,012 is subject to the same disadvantages as recognized in British Pat. No. 1,052,250.

The present invention is an improvement over the method and apparatus disclosed in British Pat. No. 1,052,250 in that the present invention produces a linear or straight line relationship between the moisture in the web and the reading of the measuring instrument whereas the method and apparatus disclosed in the aforesaid British patent produces a non-linear relationship as shown in FIG. 2 of the British patent.

SUMMARY OF THE INVENTION

It is a primary object of this invention to use microwave energy reflectance as a means of indicating and controlling moisture in web materials, particularly when the web materials have a high moisture content.

In the textile industry, high moisture or wet pickup measurement is needed in several applications.

The first is on the sizing machine or slasher, which serves to beam the yarn into a warp in final preparation for weaving and, while doing so, coat it with a starch or size compound to protect it from the abrasive action of the loom on which the warp will be woven into cloth.

In this application, it is customary to imerse the warp sheet of unwoven parallel yarns into a hot size bath containing a sizing material mixed with water. These water-soluble materials include ordinary corn starch, which has been used to size cotton yarns for many years. With the advent of new synthetic fibers, difficulty was experienced in getting the starches to adhere to and penetrate the yarn. Polyvinyl alcohol (PVA), carboxy methyl cellulose (CMC), and other synthetic materials perform better than the starches and are being used extensively now to size these yarns.

After immersion, the excess liquid is squeezed out of the warp by pneumatically-loaded rolls. The warp is then transported over a succession of steam-heated drying cylinders which evaporate the water portion, leaving the dry sizing material evenly dispersed into and onto the warp yarns.

The warp, which is wound onto a beam, is then delivered to the weave room where filling yarn is inserted to weave it into cloth. Having served its purpose of protecting the yarn from abrasion and breakage on the loom, the dry size film is subsequently washed out.

Due to the cost of the sizing material and the importance of coating the yarn with an adequate amount of it for optium weaving efficiency, it is customary to make daily de-sizing tests on yarn samples. These tests require complex laboratory procedures and require several hours of time to complete.

The de-sizing tests reveal the size pickup, expressed as a percentage by weight of the unsized yarn, usually in the range from 5 to 15 percent, depending upon fiber and other yarn parameters.

The tests reveal little about short-term inconsistency, which might be caused by uneven squeezing, size box liquid level variations, liquid temperature variations, and liquid viscosity variations. But, the tests do point up general needs for sizebox overhaul and when such work should be done.

Since the powdered sizing material is homogeneously mixed with water in a predetermined relationship, the percentage solids in the mix is known. For this reason and because the mix is uniformly applied to the yarn, a measure of the gross wet pick-up by the warp immediately after squeezing and before drying will reveal the percentage solids pickup. For example, if the mix contains 8% solids by weight and the wet pickup is measured and found to be 90% of the dry warp weight, the dry solids pickup is the product of the two or 7.2%.

Other textile applications include the use of wetting agents to enhance pickup of various materials both in slashing warps and in wet processing woven and knitted fabrics. Because the degree of wetting significantly affects subsequent pickup, it is useful to measure this as well. Other fabric applications include addition of various finishes, resins, softeners, and fire-retardant materials.

In carpet manufacturing, a similar need exists. Here, the object is to apply a rubber or synthetic material, such as Latex, as backing. By measuring the amount of liquid applied, the amount of dry material added is predictable.

In an actual test installation on a slasher, the device of this invention is continually indicating the percent solids pickup as an inference of the direct measurement of wet pickup. In addition, the device has successfully indicated uneven squeeze rolls and drop in liquid level in the size box. It is clearly responsive to the effects upon pickup by liquid temperature change and squeeze roll pressure change, the latter being obviously adaptive to automatic control of size pickup.

This device has also been tested on non-textile materials, such as wood and paper. It appears to be useable on any non-metallic, hygroscopic web or sheet material.

It is a particular advantage of this invention to incorporate both transmitter and receiver in a common housing to avoid mounting problems, such as would be encountered if the microwave energy were required to pass through the material. The advantage is even more important when it is necessary to cause the sensor to traverse back and forth across the width of the web to produce a profile measurement of moisture. This is clearly needed in many textile applications due to application roll and squeeze roll inconsistencies.

Aside from the microwave sensor, the electronic circuitry of this invention affords an advantage that would be useful with transmittance-type detectors. As will be explained, an automatic zero-setting capability permits the device to work with all materials requiring various degrees of amplification (Range) to read correctly. Regardless of amplification required for the different materials, the zero-moisture value would be set automatically. This is considered important, because it is intended that the same electronic concept be used with other sensor arrangements, both reflectance and transmittance.

From a safety standpoint, it is considered advantageous that the transmitter power is limited to 10 milliwatts. At this level, there is no radiation hazard.

It is a further object of this invention to provide apparatus which produces a linear or straight line relationship between the moisture in the web and the reading of the indicator instruments. The straight-line relationship permits the reading on the instrument to be set once to agree with actual bone-dry test determination, after which all other readings both higher and lower are readable directly. For example, when the instrument is set to read 80% moisture at midscale on a meter, 40% will be at quarter scale. The straight-line relationship also greatly facilitates reading the value digitally, which is done by converting the analog voltage appearing on the meter to a digital or numerical reading. Conventional converting devices require a straightline relationship. Of greater importance is the effect of different web densities and thicknesses. Whenever a non-linear relationship is obtained, its characteristic changes unpredictably when webs of different densities and thicknesses are tested. When the straight-line relationship is obtained, only its slope changes with changes in web density and thickness. Readings over the full moisture range are, therefore, predictable, and the instrument can be directly calibrated for each web over its full moisture range.

The straight-line relationship was obtained by experimentation. It was found that the edges of the two antennas or horns had to be in physical contact. Also, we found that only certain angles between the horns would produce the desired relationship. We selected an angle of 53°. Such a physical arrangement appeared to minimize residual energy transfer from the transmitting horn into the receiving horn. This was further minimized by a tuning screw threaded through either horn antenna wall into its interior. The depth of the tuning screw into the horn critically affects the residual energy transfer. The adjustment must be made with either no web or a very dry web over the device.

It is very important to the intended operation of the equipment of this invention that the residual energy transfer be minimized. This is done, because the receiver gain must be varied over a wide range to accommodate a wide range of web densities and thicknesses. With appreciable residual energy transfer present, changes in receiver gain would affect the zero reading, since any residual energy transfer at zero would be amplified to varying degrees when the receiver gain is changed. Ideally, changes in receiver gain will merely change the slope of the straight-line relationship between moisture and instrument reading, having no effect at zero.

This ideal characteristic is finally achieved by the zero-offset circuitry subsequently described. The dependence upon this circuitry is greatly reduced by the mechanical effects described.

In its preferred form, the device has two adjustable controls on its front panel for operator adjustment. First, the receiver gain is adjusted for mid-scale reading on a meter. The gain control is calibrated, and the setting is recorded for future use. This allows for the reflectance differences of webs of different densities and thicknesses. Second, a calibrated control is adjusted to cause a corresponding digital readout to indicate the estimated moisture either in terms of percentage of the dry weight of the web or in terms of absolute moisture, such as "ounces per square yard" or "grams per square meter." This latter setting is recorded along with the digital readout. A physical sample of the web is immediately taken and tested for actual moisture by the bone-dry test method. The digital adjustment is then changed by the exact difference between the estimated value and the actual value. The two control settings are then referred to in the future when the same web material is again processed.

BRIEF DESCRIPTION OF THE DRAWINGS

With the foregoing more important objects and features in view and such other objects and features which may become apparent as this specification proceeds, the invention will be understood from the following description taken in conjuction with the accompanying drawings, in which like characters of reference are used to designate like parts and in which:

Referring now to FIG. 1, the microwave moisture indicator portion of the present invention in generally indicated by the reference numeral 100. Looking first at the upper left hand corner of FIG. 1, a sealed microwave transducer enclosure 7 is shown positioned beneath a moving web 10 of material whose moisture content is being monitored. The microwave transducer enclosure 7 is a box enclosure having an inner top plate 8 which is provided with a cut-out opening 8a equal in area to the combined areas of the openings of a microwave transmitting horn antenna 3 and of a receiving horn antenna 6. A low-dielectric material plate 9 is superimposed on the plate 8 and covers the cut-out opening 8a to protect the microwave transducer from the operational environment. The microwave transmitting horn antenna 3 and the microwave receiving horn antenna 6 are secured to the plate 8 with their open ends flush with the upper surface of the plate 8. The horns 3 and 6 are angularly mounted within the enclosure 7 to subtend equal angles with respect to a plane normal to the plate 8 and equi-distant between the two horns. An X-band Gunn oscillator 1 with its integral Gunn diode 2 is coupled to the transmitting horn antenna 3 to transmit microwave radiation in the direction of the web 10. An X-band detector 4 with its integral Schottky diode 5 is coupled to the horn antenna 6. Microwave radiation reflected from the web 10 is detected by the detector 4. FIG. provides an enlarged, more detailed view of the transducer enclosure 7 than is seen in FIG. 1.

Figure 1:
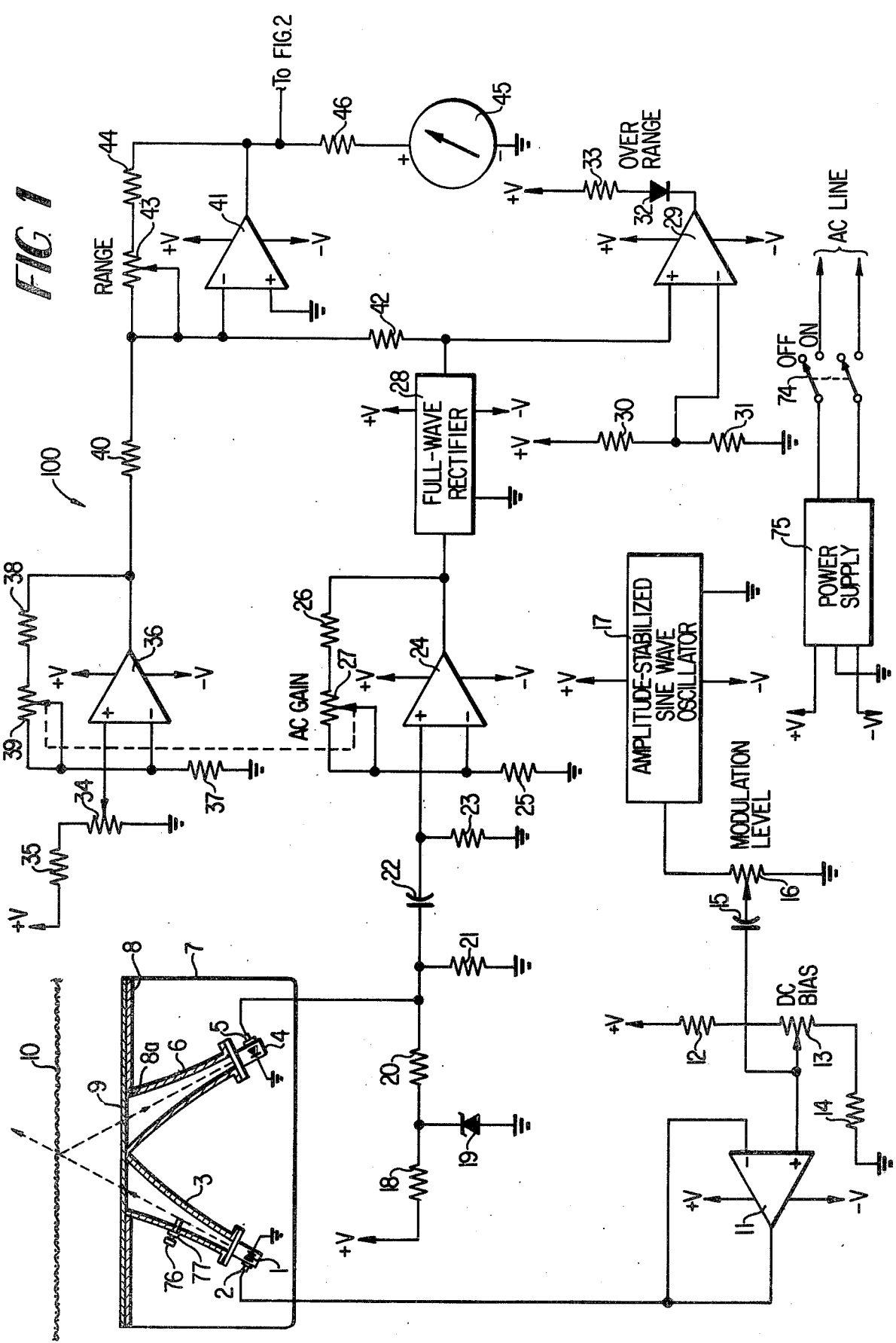
FIG. 1 is a partial block and partial schematic diagram of a microwave moisture measuring and indicating circuit constructed in accordance with the principles of the present invention.

Looking now at the lower center portion of FIG. 1, a conventional amplitude-stabilized sine-wave oscillator 17 provides the modulation source for the transmitting Gunn oscillator 1. The oscillator frequency is not critical and only serves as a more easily recoverable signal than the 10.525 GH$_z$ signal transmitted by the X-band oscillator 1. In practice, 10K H$_z$ was chosen as a suitable frequency. The modulation level potentiometer 16 allows precise adjustment of the sine-wave amplitude which is coupled via capacitor 15 to the input of a voltage-follower buffer 11.

The X-band Gunn oscillator 1 requires a d-c bias voltage to operate. The DC bias potentiometer 13 and resistors 12 and 14 provide means to set this bias precisely.

After the modulated microwave signal contacts the material 10, it is reflected back into the receiver antenna 6 and detected by the Schottky diode 5. The modulated signal, thus detected, is a 10K H$_z$ sine wave, the amplitude of which is directly proportional to the amount of water present in the material.

A d-c bias current of approximately 32 microamperes is required for the Schottky diode. Resistors 18, 20, and 21, along with zener diode 19, form a regulated supply to furnish the required bias current from the power supply 75.

The detected signal from the microwave detector 4 is next coupled via capacitor 22 to the plus (+) input of operational amplifier 24. Resistor 23 serves as an input load resistor for the amplifier. Amplifier 24 is configured in the standard non-inverting mode. Amplifier gain is controlled by the a-c gain potentiometer 27 and resistors 25 and 26. The gain of this amplifier must be adjustable over a broad range due to the wide range of warp and fabric weights encountered. Lower gain settings are employed with most fabrics and dense warps while higher settings are required with very light weight fabrics and most warps. At these higher gain settings, a small signal is present at the output of amplifier 24 when there is no material over the transducer. This signal is due to a constant leakage of the microwave energy along the lower surface and through the cover plate 9 from transmitting horn antenna 3 into the receiver horn antenna 6. Since this signal is an a-c signal, a d-c offset at the input of amplifier 24 will not effectively cancel it and since the amplitude of this signal is a function of amplifier gain, any compensating means must be variable and in proportion to the gain setting of amplifier 24. Therefore, an effective means of cancelling this signal is to do so with a gain-controlled d-c voltage after the main a-c signal is converted to d-c.

The signal conversion from a-c to d-c is accomplished by the full wave rectifier 28. This is a precision operational amplifier-based converter of standard design, wherein the d-c output voltage is negative and is equal to the average value of the a-c input voltage.

Returning to the problem of offsetting the signal present with no material over the transducer, a separate amplifier 36 is employed with identical operating characteristics as amplifier 24. In other words, the value of each component equals its counterpart associated with amplifier 24. Resistor 37 equals resistor 25, resistor 38 equals resistor 26, and potentiometer 39 equals potentiometer 27. Also, the two potentiometers, 27 and 39, are ganged on the same shaft so that varying one varies the other the same amount.

The zero potentiometer 34 and series resistor 35 provide an adjustable positive input voltage to amplifier 36. Therefore, the zero potentiometer 34 can be set so that the positive output voltage from amplifier 36 is equal to the negative output voltage from the full wave rectifier 28 when no material is over the transducer. These two voltages will change if the ganged combination of potentiometers 27 and 39 are adjusted, but they will remain equal. Since these two outputs are connected via equal resistors 40 and 42 to the summing node of inverting amplifier 41, the net input current to this amplifier is zero, thereby providing an effective means fo cancelling the residual leakage of microwave energy from horn 3 to horn 6, regardless of a-c gain setting.

Figure 3:
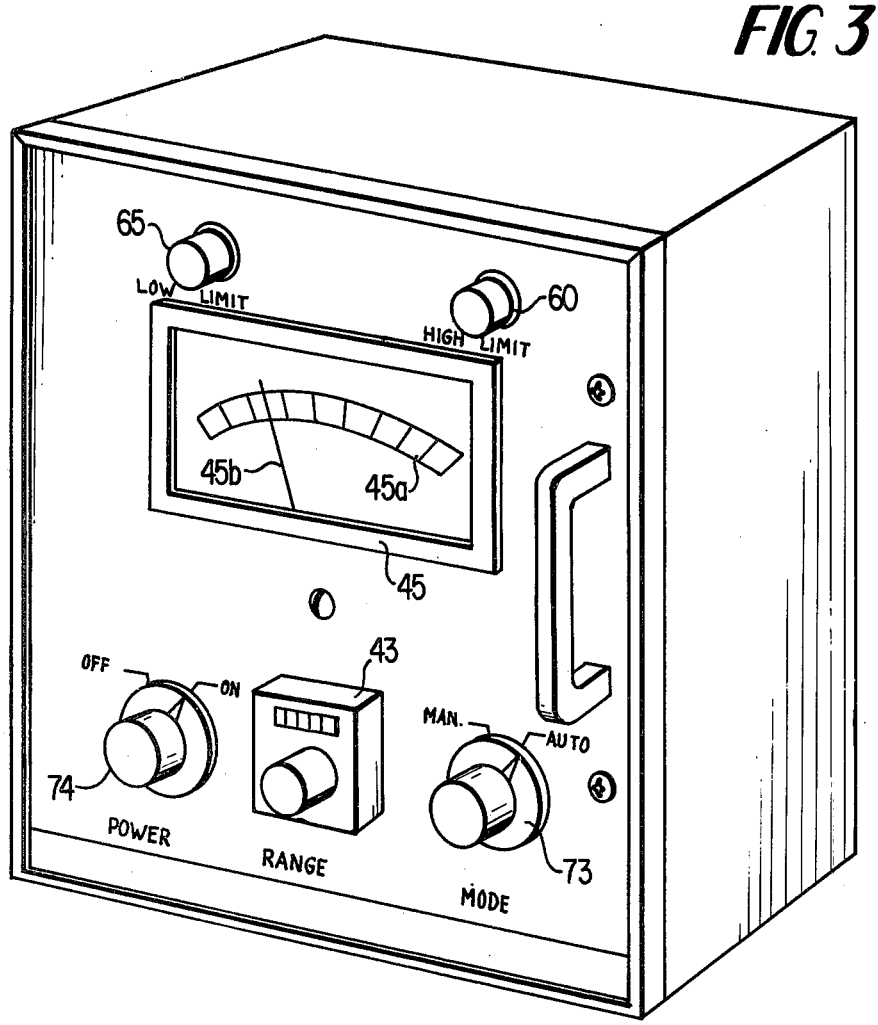
FIG. 3 is a perspective view of the indicating and control front panel and cabinet of the present invention.
Figure 4:
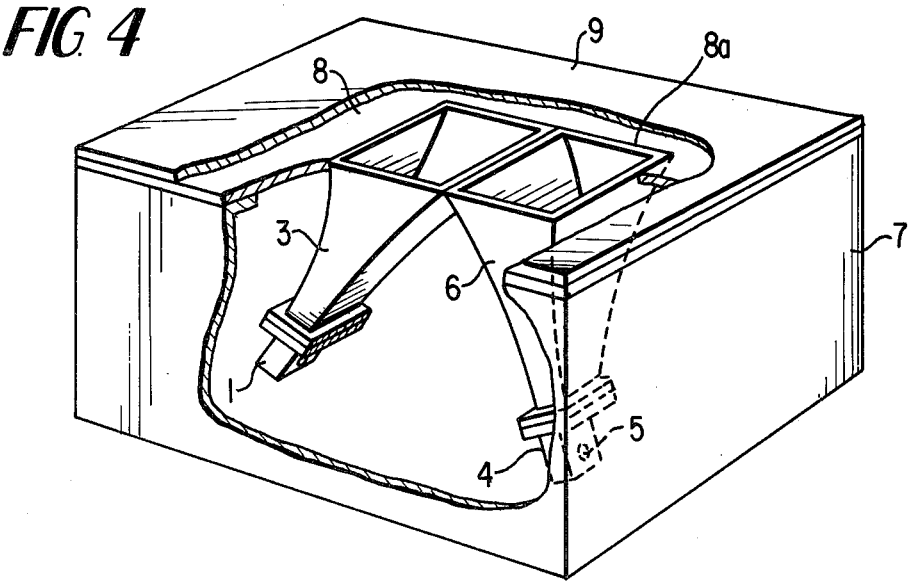
FIG. 4 is a perspective cutaway view of the microwave transducer mounting enclosure of the present invention.

A range potentiometer 43 and series resistor 44 form the d-c gain control elements of amplifier 41. The purpose of the range control 43 is to set the reading on the d-c microammeter 45 to agree with the percentage moisture or solids actually in the material 10. The range control is calibrated 0–999 units. Once the correct setting is determined for a particular warp or fabric style, the numerical reading on the range control can be recorded for future use. Resistor 46 serves to limit the current through the microammeter 45. FIG. 3 shows the meter 45 with calibrated scale 45a. The position of the meter pointer 45b is then indicative of the moisture or solids value. Since the relationship between current and moisture is linear and since the zero position is automaticaly set regardless of material weight or thickness, physical correlation at only one point is necessary to cause the readout to be correct over the full meter range. As an alternate to the analog meter, a suitable digital panel meter (DVM) could be employed with the range control serving as a scale factor adjustment to cause the digital readout to agree with measured values of moisture or solids in the material.

One remaining section of the measuring circuit is the comparator 29 and associated parts. As previously mentioned, the required gain adjustment span of the a-c amplifier 24 is quite broad owing to the extreme weight range of warps and fabrics encountered. It is possible to have too high a gain setting for the a-c amplifier and a correspondingly low setting for the range potentiometer 43. The purpose of the comparator 29 is to warn the operator of this condition. With a reference voltage at the junction of resistors 30 and 31 equal to the maximum linear (non-saturated) output from the full-wave rectifier 28, the LED (light emitting diode) 32 identified as Over Range will give a visual indication if this level is exceeded. Resistor 33 provides current limiting for the LED.

Figure 2:
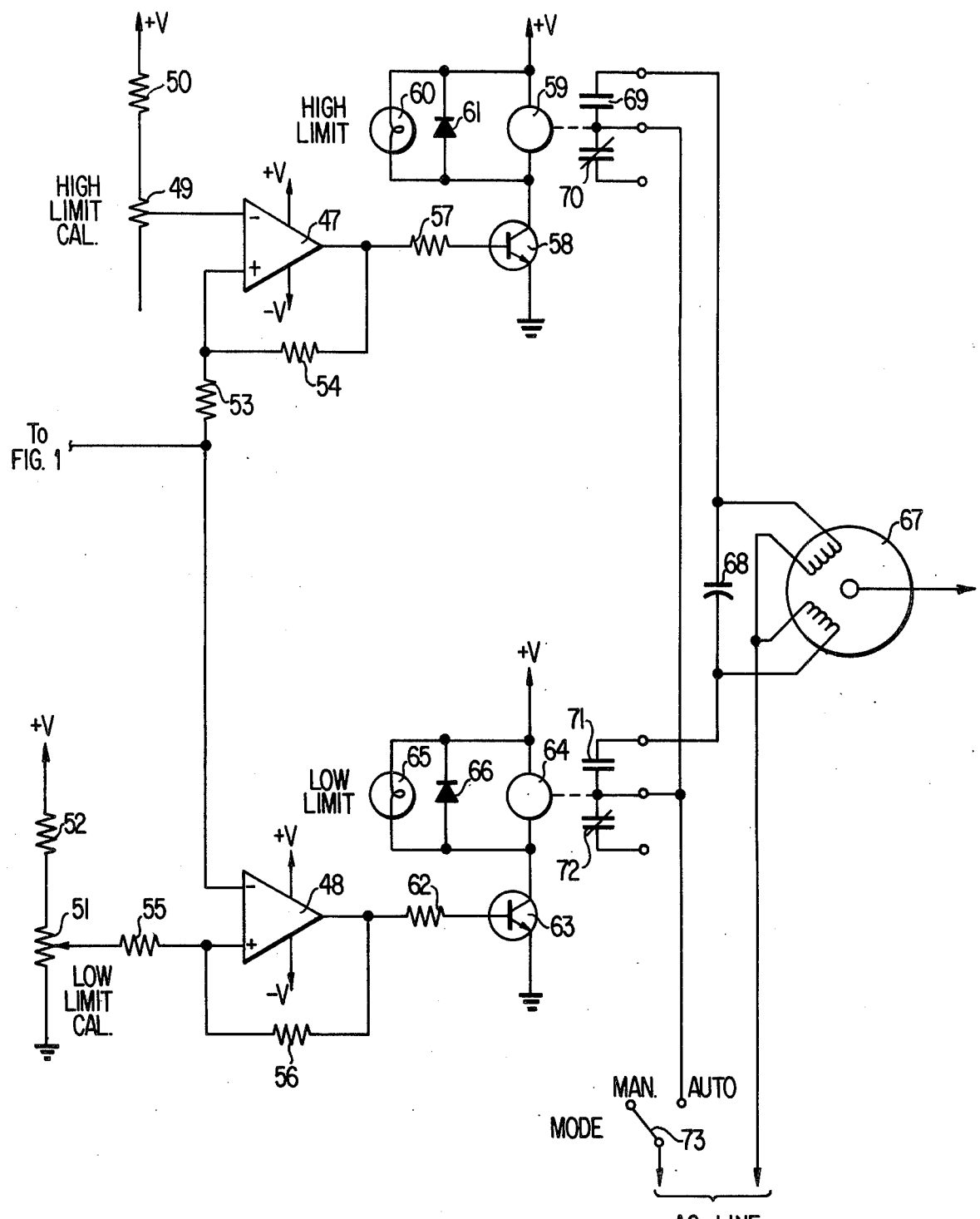
FIG. 2 is a schematic diagram of the moisture control circuit portion of the present invention to be used in conjunction with the circuit illustrated in FIG. 1.

The output of amplifier 41 also furnishes the required signal for the controlling portion of the instrument shown in FIG. 2. This signal is fed to two comparators 47 and 48. At the high limit comparator 47, the signal is applied, via resistor 53 to the + input. Resistors 53 and 54 provide slight hysteresis for the comparator. The high limit calibration (High Limit Cal.) potentiometer 49 and series resistor 50 provide means for setting a voltage, proportional to a point on the meter scale 45a, above which control action is desired. When the voltage at the + input of comparator 47 exceeds the voltage at the − input, the output of the comparator goes high, thereby energizing transistor 58 via base current-limiting resistor 57. This, in turn, grounds the lower side of relay coil 59, lamp 60, and the anode of diode 61 causing the lamp to give a visual indication that the limit was exceeded and energizing the relay. The normally open contacts 69 make and voltage is applied to one winding of the two-coil reversible control motor 67 if the Mode switch 73 is positioned to Auto.

Operation of the low limit comparator 48 is similar, except that the inputs to the comparator are reversed. This results in operation of relay 64 and lamp 65 when the reading on the meter falls below the value set on the low limit calibration (Low Limit Cal.) potentiometer 51. Resistors 55 and 56 provide hysteresis for this comparator in like manner of resistors 53 and 54.

Diodes 61 and 66 provide return paths for the inductive relay coil discharges when either transistor 58 or 63 turns off. Capacitor 68 provides the required phase shift for the control motor 67.

The entire unit is powered by a conventional dual regulated power supply 75 (shown at the bottom of FIG. 1) operated, via a power, off-on switch 74, from standard a-c lines.

Referring back to FIG. 1, a tuning screw 76 is shown threaded in the transmiter horn 3 and locked in adjusted position by a jam nut 77. The tuning screw 76 helps to minimize residual energy transfer from the transmitting horn 3 into the receiving horn 6. The screw 76 may be threaded through either horn antenna wall into the interior of the horn. The depth of the tuning screw into the horn critically affects the residual energy transfer. The adjustment of the screw must be made when either no web, or a very dry web is over the transducer housing 7 to minimize the residual energy transfer.

While in the foregoing there has been described and shown a preferred embodiment of the invention, various modifications and equivalents may be resorted to within the spirit and scope of the invention as claimed.

What is claimed is:

1. A microwave moisture meter for measuring the moisture content of a moving web of moisture absorbent material comprising a microwave transmitter means for transmitting an a-c modulated microwave signal of a selected frequency and energy level toward the moving web, a microwave receiver means for receiving microwaves reflected from the moving web, said microwave transmitter means including a directional transmitter antenna horn whose axis is directed toward the web at the angle of incidence of the transmitted microwaves, said microwave receiver means including a directional receiver antenna horn on the same side of the web as the transmitter antenna horn and whose axis is directed toward the web at the angle of reflectance of the transmitted microwaves which are reflected from the web and a microwave detector means for detecting the reflected microwave signal and producing an a-c output signal whose amplitude is directly proportional to the amount of moisture in the web, an adjustable gain amplifier means for amplifying the a-c output signal from said detector means, a signal conversion means for converting the amplified a-c signal to a d-c output signal which is equal to the average value of the a-c signal input to the conversion means, zero offsetting means for offsetting the signal detected by said detector when no material is in front of the transmitter and receiver horn, said zero setting means being adjustable to produce a d-c output signal equal to and of opposite polarity to the d-c signal produced by said signal conversion means when no material is over the microwave transmitter and receiver horn, invertor amplifier means having a summing input node for summing the output signals of said conversion means and said offsetting means and for amplifying the summation signal and producing a d-c moisture indicating signal which is directly proportional to the moisture content of said moving web of material, and indicator means responsive to said d-c moisture indicating signal for indicating a quantity which is a function of the moisture content of said web.

2. The microwave moisture meter according to claim 1 wherein each of said transmitter and receiver horns has a narrow end, a wide open end, and encompassing wide walls which diverge outwardly from said narrow end to said wide open end, mounting means for mounting the open ends of said transmitter and receiver horns in side-by-side contiguous relationship, said transmitter and receiver horns being angled with respect to each other so that the included angle between their axes is at a selected optimum value in order to minimize residual energy transfer from the transmitting horn into the receiving horn.

3. The microwave moisture meter of claim 2 wherein said mounting means includes a mounting plate having an opening therein, in which the open ends of said transmitter and receiver horns are mounted, an enclosure enclosing said transmitter and receiver horns, said mounting plate forming an inner top wall of said enclosure, said enclosure having an outer top plate of low dielectric material covering said mounting plate and the open ends of said transmitter and receiver horns.

4. The microwave moisture meter of claim 1 wherein at least one of said transmitter and receiver horns has a tuning screw adjustably mounted therein.

5. The microwave moisture meter of claim 1 wherein said transmitter means includes an X-band transmitting oscillator coupled to said transmitter horn, an amplitude-stabilized sine-wave oscillator providing an a-c modulation source for said X-band transmitting oscillator, and modulation level adjusting means for adjusting the sine-wave amplitude of the modulation signal supplied by said a-c modulation source to said X-band transmitting oscillator.

6. The microwave moisture meter of claim 5 wherein said X-band transmitting oscillator is an X-band Gunn oscillator having an integral Gunn diode.

7. The microwave moisture meter of claim 6 wherein said microwave transmitter means further includes a voltage-follower buffer interposed in circuit between said X-band transmitting oscillator and said modulation level adjusting means, and an adjustable d-c bias voltage source providing d-c bias voltage to operate said Gunn oscillator, said d-c bias voltage and said sine-wave modulation signal being fed to said Gunn oscillator through said voltage-follower buffer.

8. The microwave moisture meter of claim 1 wherein said adjustable gain amplifier means is a first operational amplifier configured in a non-inverting mode and comprising a positive input terminal, a negative input terminal, an output terminal, a resistor connecting said negative input terminal to ground and a series resistor network, connecting said output terminal to said negative input terminal and including an adjustable a-c gain potentiometer, a coupling network means for coupling the a-c output signal from said detector means to said positive terminal of said first operational amplifier, said zero offsetting means comprising a separate operational amplifier with substantially identical operating charcteristics as said first operational amplifier, said separate operational amplifier having positive and negative input terminals and an output terminal, a resistor connecting said negative input terminal to ground and being of equal value as the corresponding resistor is said first operational amplifier, a series resistor network connecting said output terminal to said negative input terminal and having resistor components of substantial equal value to corresponding components in said resistor network of said first operational amlifier, said resistor network of said separate operational amplifier including an adjustable gain potentiometer which is ganged to the adjustable gain potentiometer of said first operational amplifier so that varying one varies the other the same amount, a voltage divider network means including a zero potentiometer for supplying as zeroing input voltage to the positive terminal of said separate operational amplifier.

9. The microwave moisture meter of claim 1 wherein said invertor amplifier means includes an adjustable range potentiometer for adjusting the gain thereof and thereby setting the reading on said indicator means to agree with the percentage moisture or other quantity which is a function thereof actually in the web material.

10. The microwave moisture meter of claim 9 wherein said indicator means is an analog meter.

11. The microwave moisture meter of claim 10 together with an overrange indicator means for detecting and indicating when the gain setting of said adjustable gain amplifier means exceeds a predetermined level.

12. The microwave moisture meter of claim 1, together with control means responsive to said d-c moisture indicating signal for taking correstive action to vary the moisture content of said web when predetermined high and low moisture conditions are reached so as to maintain the moisture content within predetermined limits.

* * * * *